United States Patent

Remans et al.

[11] Patent Number: 5,959,163
[45] Date of Patent: Sep. 28, 1999

[54] PROCESS FOR THE PREPARATION OF 1,4-BUTENEDIOL FROM EPOXYBUTENE

[75] Inventors: Thomas J. Remans, Leuven; Pierre A. Jacobs, Gooik; Johan Martens, Huldenberg, all of Belgium; Dominicus A. G. van Oeffelen; Mathias H. G. Steijns, both of Terneuzen, Netherlands

[73] Assignee: The Dow Chemical Company, Midland, Mich.

[21] Appl. No.: 08/923,146

[22] Filed: Sep. 4, 1997

[51] Int. Cl.$^6$ ...................................................... C07C 29/56
[52] U.S. Cl. ............................................ 568/857; 568/860
[58] Field of Search ...................................... 568/857, 860

[56] References Cited

U.S. PATENT DOCUMENTS

| | | | |
|---|---|---|---|
| 2,911,445 | 11/1959 | Friederich et al. | 260/635 |
| 2,953,605 | 9/1960 | Hort | 260/635 |
| 4,209,651 | 6/1980 | Prichard | 568/861 |
| 4,234,747 | 11/1980 | McIndoe | 568/857 |
| 4,384,416 | 5/1983 | Kanzelberger | 40/10 D |
| 5,117,012 | 5/1992 | Stavinoha, Jr. et al. | 549/538 |
| 5,166,372 | 11/1992 | Crocco et al. | 549/531 |
| 5,463,144 | 10/1995 | Powell et al. | 568/867 |
| 5,530,167 | 6/1996 | Tustin | 568/857 |

FOREIGN PATENT DOCUMENTS

| | | |
|---|---|---|
| 0 190 609 | 1/1990 | European Pat. Off. . |
| 57 002 227 | 7/1982 | Japan . |

OTHER PUBLICATIONS

Abstract of DE 2 734 240.
Abstract of DE 4 342 030.
Abstract of DE 4 429 699.
Abstract of DE 4 429 700.
Abstract of JP 49 049 910.
Abstract of JP 53 127 405.
Abstract of JP 54 061 108.
Abstract of JP 54 073 710.
Abstract of JP 59 084 831.
Abstract of JP 62 054 788.

*Primary Examiner*—John Kight
*Assistant Examiner*—Charanjit S. Aulakh

[57] ABSTRACT

Disclosed is a process for the preparation of 2-butene-1,4-diol comprising contacting a mixture of water and 1,2-epoxy-3-butene with a catalyst comprising a metal halide, zeolite and a non-protic solvent.

14 Claims, No Drawings

PROCESS FOR THE PREPARATION OF 1,4-BUTENEDIOL FROM EPOXYBUTENE

This invention relates to a selective catalyst comprising a metal halide on a zeolite and use of said catalyst for the conversion of epoxybutene to 1,4-butenediol.

A substance of prime importance to the chemical industry is 1,4-butenediol (BDO) which has value in polymer chemistry including polyester and polyurethane production, in the production of compounds having pharmaceutical properties, and in the preparation of the industrial solvent tetrahydrofuran. For the present, the principle industrial source of BDO is through the reaction of formaldehyde with acetylene so provide an intermediate which on hydrogenation gives the BDO. As acetylene is a gas and requires attentive handling to avoid risk of explosion there is a desire to develop alternative manufacturing procedures overcoming the need to use acetylene.

Alternative chemistry leading to the obtaining of 1,4-butanediol does exist. For example the manufacture of 1,4-butanediol starting from 1,3-butadiene, a widely available industrial feedstock, and involving the steps of (1) converting 1,3-butadiene to 1,2-epoxy-3-butene; (2) hydrolyzing 1,2-epoxy-3-butene to 3-butene-1,2-diol; (3) isomerizing 3-butene-1,2-diol to 2-butene-1,4-diol; and (4) finally hydrogenating 2-butene-1,4-diol to 1,4-butanediol. For Step 1, 1,3-butadiene can be converted to 1,2-epoxy-3-butene by an appropriate epoxidizing agent such as, for example, hydrogen peroxide in the presence of an acid catalyst such as disclosed in DE 2,734,240; oxygen in the presence of a silver catalyst such as disclosed in U.S. Pat. No. 5,117,012; hydrogen peroxide/alcohol/water mixtures in the presence of an organorhenium catalyst such as disclosed in U.S. Pat. No. 5,166,372; or hydrogen peroxide in the presence of Ti/Si catalysts as disclosed in European Patent 190,609. For Step 2, 1,2-epoxy-3-butene can be hydrolyzed to obtain 3-butene-1,2-diol by an appropriate hydrolyzing agent. Such agents and procedures include acid catalyzed solvolysis such as disclosed in the publication Tetrahedron Asymmetry page 15–16, Vol. 6, 1995; water as disclosed in DE 4,342,030; water in the presence of $SiO_2/TiO_2/F$ as disclosed in DE 4,429,699; water in the presence of rhenium oxide ($Re_2O_7$) as disclosed in DE 4,429,700. For Step 3; isomerization of 3-butene-1,2-diol to 2-butene-1,4-diol can be in the presence of water-soluble mercuric salts employed under acidic conditions such as disclosed in U.S. Pat. No. 2,911,445; metal iodides such as disclosed in JP 59-084,831 and JP 82-002,227; and calcium compounds such as disclosed in JP 79-073,710. For Step 4; 2-butene-1,4-diol can be hydrogenated by procedures employing hydrogen over nickel catalysts such as disclosed in JP 53-127,405; JP 62-054,788; JP 74-049,910; JP 79-061,108. However such alternative chemistry has not found industrial acceptance due to comprising multiple step procedures, expensive catalysts, or exhibiting low conversion/selectivity yields.

In U.S. Pat. No. 5,530,167, it is proposed to convert 1,2-epoxy-3-butene directly to 2-butene-1,4-diol by a hydrolysis procedure in the presence of a catalyst comprising a catalyst support material and copper in a positive valence state. While this procedure provides for a mixture rich in 2-butene-1,4-diol there is still a need to provide for the production of 2-butene-1,4-diol in improved yields and selectivity.

Accordingly it is desirable to develop a simpler and more effective procedure for the manufacture of 2-butene-1,4-diol. With consideration to the above proposed steps, it would be highly desirable to develop a procedure which permits the conversion of 1,2-epoxy-3-butene directly to 2-butene-1,4-diol with attractive yields and selectivity.

As a result of the present studies an alternative catalyst system for use in hydrolysis of 1,2-epoxy-3-butene directly to 2-butene-1,4-diol has been developed.

SUMMARY OF THE INVENTION

The present invention provides an effective means for the selective hydrolysis of 1,2-epoxy-3-butene directly to 2-butene-1,4-diol with attractive conversion rates and improved selectivity.

In one aspect, this invention relates to a process for the preparation of 2-butene-1,4-diol which comprises contacting a mixture of water and 1,2-epoxy-3-butene with a catalyst comprising a metal halide, a zeolite and a non-protic solvent.

DETAILED DESCRIPTION OF THE INVENTION

The catalyst system of the present invention is a combination of a zeolite material with a metal halide in conjunction with an aprotic solvent. Such a system in the presence of water can be used to directly hydrolyze/isomerize 1,2-epoxy-3-butene to 2-butene-1,4-diol.

The metal halide of preference is an iodide where the cation is an alkali or alkali earth metal from Group 1 or 2, or a transition metal from Group 11 or 12 of the Periodic Table of the Elements. Advantageously for ease of handling and eventual solubility, the cation when selected from a Group 1 or 2 metal element include sodium, potassium, magnesium and calcium, and when from a Group 12 metal include zinc. A preferred cation in the present invention is potassium. The preferred metal halide is potassium iodide.

The ratio of metal halide to epoxy substrate in the present process is generally from about 5:1 to 1:5 and preferably from 3:1 to 1:3. More preferably the halide to epoxy ratio is 1:1.

Another component of the catalyst system, which contains acidic properties, is an aluminosilicate mineral commonly referred to as a zeolite. Zeolites are crystalline hydrated aluminosilicates of Group 1 and 2 elements, including sodium, potassium, magnesium, calcium, strontium and barium, constructed of "infinitely extending" networks of $AlO_4$ and $SiO_4$ tetrahedra joined by the sharing of oxygen atoms. They may be represented by the empirical formula:

$$M_{n/2} \cdot Al_2O_3 \cdot xSiO_2 \cdot yH_2O$$

where X is usually greater than 2, and n is the cation valence. Zeolites have been extensively studied and classified according to the topology of the aluminosilicate framework and their chemical composition, notably the Si/Al ratio. Zeolite types X and Y have a cubic unit cell which contains 192 $SiO_4$ and $AlO_4$ tetrahedra; the relationship between the number of tetrahedral Al atoms ($N_{Al}$) and the Si/Al ratio is

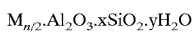
$$N_{Al} = 192/(1+R) \quad R = N_{Si}/N_{Al}$$

where $N_{si}$ is the number of tetrahedral Si atoms. The number of aluminum atoms in the unit cell of the X zeolite varies between 96 and 77, and R between 1 and 1.5. In Y zeolites, the number of aluminum atoms in the unit cell varies between 76 and 48, and R between 1.5 and 3.0. In the present invention the catalyst support is preferably a Zeolite Y, and especially an ultra-stable zeolite Y with a Si/Al ratio of from about 5:1 to about 100:1. Exemplary of commercially zeolites supports suitable for use in the present invention include the product CBV-780 available from Pennsylvania Quartz Corporation and understood to be a Y type zeolite with a Si/Al ratio of about 40:1.

When the reaction of the current process is carried out in the liquid phase, the amount of zeolite is generally present in a concentration of about 1 to 50 weight percent, preferably about 5 to 30 weight percent.

In a highly preferred embodiment of this invention, the metal halide and zeolite components of the catalyst comprise potassium iodide and an ultra stable Y type zeolite. Use of such a metal halide/zeolite with an aprotic solvent has been found to be very beneficial to the yield of 1,4-butenediol from 1,2-epoxy-3-butene. It is noted that when a mineral acid is used in place of the zeolite, the yields are distinctly inferior.

The catalyst system further comprises an aprotic, or non-protic, solvent. Exemplary of such solvents include ketones such as, for example, propan-2-one and butan-2-one; ethers such as dialkyl ethers where the alkyl groups independently contain from 1 to 4 carbon atoms and exemplified by, for example, diethyl ether; and diethers such as, for example, dimethoxyethane, or cyclic ethers such as, for example, tetrahydrofuran or 1,4-dioxane. A highly preferred solvent is dimethoxyethane, the use of which in the present process leads to an unexpectedly high selectivity.

The weight ratio of solvent to water is generally greater than 1. Typically the solvent to water ratio is about 5:1, preferably about 3:1. More preferably the ratio is about 2:1.

The reactive materials (water and epoxy) may be employed in the process in a water to epoxy ratio of about 100:1 to 1:1. Preferably the ratio is about 10:1 to about 60:1. More preferably the water to epoxy ratio is about 20:1 to 40:1.

The process conditions for temperature and pressure are generally set to maintain the substrate and catalyst in the liquid phase. The temperature is typically 0° C. to 120° C., preferably about 5° C. to 100° C. More preferably the temperature is about 10° C. to 90° C. The pressure used in the present process will generally depend on the selected process temperature. For example, at 75° C., the pressure will be about 0.3 MPa. The process can be done in a batch mode, semi-batch or as a continuous process.

The following examples illustrate the present invention and the manner by which it can be practiced but, as such, should not be construed as limitations upon the overall scope of the invention.

General Experimental

Hydrolysis of the epoxy is performed in stainless steel batch reactors of PARR Instruments Corporation, type 452 HC with a volume of 100 mL.

Reaction products are measured on a Hewlett-Packard gas chromatograph of the type HP 5890 Series II equipped with a flame ionization detector using a wall coated open tubular column with polydimethylsiloxane coating (CP-Sil-5 B from Chrompack).

EXAMPLE 1

To a reaction vessel was added 1.4 g of 1,2-epoxy-3-butene (butadiene monoxide); 14.4 g of water; 3.32 g potassium iodine; 0.4 g of sulfuric acid; and 16 g of acetone. The conversion and selectivity for 2,butene-1,4-diol (at 75° C.) for this and modified conditions are given in Table I.

TABLE I

| Modification | Conversion (%) | Selectivity for 2-butene-1,4-diol (%) |
|---|---|---|
| None[1] | 99% (8 h) | 38% (8 h) |
| Without iodide[1] | 60% (23 h) | 8% (23 h) |
| Without sulfuric acid[1] | 25% (23 h) | 4% (23 h) |
| Sulfuric acid replaced by zeolite[2] US-Y Si/Al = 10 | 93% (28 h) | 65% (28 h) |
| Sulfuric acid replaced by zeolite[2] H-Beta Si/Al = 10.8 | 97% (28 h) | 62% (28 h) |

[1]Comparative example, not part of the present invention
[2]Examples of the present invention. Zeolite obtained from Pennsylvania Quartz Corporation.

These results show that replacement of the sulfuric acid with a zeolite, greatly improved the selectivity.

EXAMPLE 2

To determine the effect of aprotic organic solvents on conversion, a reaction mixture of 10 mmol 1,2-epoxy-3-butene; 10 mmol potassium iodide; 0.2 g zeolite US-Y (Si/Al ratio of 10); 7.2 g water and 20 mL of various solvent were prepared (Table II). The reaction temperatures were 75° C.

TABLE II

| Solvent | Conversion after 6 h (%) | Selectivity (%) at maximum conversion for: solvolysis | 2-butene-1,4-diol |
|---|---|---|---|
| acetone | 8 | 18 | 55.5 |
| ethyl ether | 10 | 0 | 66 |
| 1,4-dioxane | 12 | 0 | 68.5 |
| 1,2-dimethoxyethane | 97.8 | 0 | 73.9 |

These results show that ketones and ethers are suitable aprotic solvents for use in the present process.

EXAMPLE 3

The influence of the water concentration on the formation and hydrolysis of 4-iodo-2-butene-1-ol is given in Table III. The results were obtained by adding to a reaction vessel, 10 mmol 1,2-epoxy-3-butene; various amount of water; 1.66 g potassium iodide; 0.2 g zeolite US-Y (Si/Al ratio of 10); 1,2-dimethoxyethane; temperature =75° C.

TABLE III

| mmol water | Conversion after 3 h (%) | Selectivity (%) at 80% conversion for: 2-butene-1,4-diol | 4-iodo-2-butene-1-ol |
|---|---|---|---|
| 400 | 81.7 | 69.2 | 12.5 |
| 200 | 56.9 | 57.2 | 21.2 |
| 100 | 52.6 | 44.7 | 31.8 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for the preparation of 2-butene-1,4-diol which comprises contracting a mixture of water and 1,2-epoxy-3-butene with a catalyst consisting essentially of a metal iodide, an acidic zeolite and a non-protic solvent wherein the metal is an alkali metal, alkali earth metal from Group 1 or 2, a transition metal from Group 11 or Group 12 of the Periodic Group of the Elements, or a mixture thereof, the zeolite is a crystalline hydrated aluminosilicate of Periodic Group 1 or Group 2 and the non-protic solvent is an ether or ketone.

2. The process of claim 1 wherein the cation is selected from the group consisting of Periodic Group 1 or 2 metal element including sodium, potassium, magnesium and calcium.

3. The process of claim 1 wherein the cation is selected from Periodic Group 12.

4. The process of claim 3 wherein the Group 12 metal cation is zinc.

5. The process of claim 4 wherein the cation is potassium.

6. The process of claim 1 wherein the metal halide is potassium iodide.

7. The process of claim 1 wherein the zeolite is represented by the empirical formula:

$$M_{n/2} \cdot Al_2O_3 \cdot xSiO_2 \cdot yH_2O$$

where X is greater than 2, and n is the cation valence.

8. The process of claim 7 wherein the relationship between the number of tetrahedral Al atoms ($N_{Al}$) and the Si/Al ratio is $$N_{Al} = 192/(1+R) \quad R = N_{Si}/N_{Al}$$

where $N_{Si}$ is the number of tetrahedral Si atoms, and the number of aluminum atoms in the unit cell is from about 96 to about 77, and R is between 1 and 1.5.

9. The process of claim 7 wherein the relationship between the number of tetrahedral Al atoms ($N_{Al}$) and the Si/Al ratio is $$N_{Al} = 192/(1+R) \quad R = N_{Si}/N_{Al}$$

where $N_{Si}$ is the number of tetrahedral Si atoms, and the number of aluminum atoms in the unit cell is from about 76 to about 48, and R is between 1.5 and 3.0.

10. The process of claim 7 where the catalyst support is a Zeolite with a Si/Al ratio of from about 5:1 to about 100:1.

11. The process of claim 10 wherein the metal halide is potassium iodide.

12. The process of claim 1 wherein the non-protic solvent in an ether.

13. The process of claim 12 wherein the ether is 1,4-dioxane, dimethoxyethane, or diethylether.

14. The process of claim 11 wherein the non-protic solvent is dimethoxyethane.

* * * * *